(12) United States Patent
DeVore

(10) Patent No.: US 6,508,783 B2
(45) Date of Patent: Jan. 21, 2003

(54) ULTRASOUND METHOD FOR REVASCULARIZATION AND DRUG DELIVERY

(75) Inventor: Lauri J. DeVore, Seattle, WA (US)

(73) Assignee: Scimed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/808,624

(22) Filed: Mar. 14, 2001

(65) Prior Publication Data

US 2002/0133101 A1 Sep. 19, 2002

(51) Int. Cl.[7] .............................. A61B 17/20; A61N 1/30
(52) U.S. Cl. ........................ 604/22; 604/19; 607/119; 607/122
(58) Field of Search ...................... 604/19–22; 607/115, 607/119, 120, 122

(56) References Cited

U.S. PATENT DOCUMENTS

| | | | |
|---|---|---|---|
| 4,790,311 A | | 12/1988 | Ruiz |
| 5,318,014 A | * | 6/1994 | Carter ......................... 604/22 |
| 5,588,432 A | | 12/1996 | Crowley |
| 5,607,421 A | | 3/1997 | Jeevanandam et al. |
| 5,681,308 A | | 10/1997 | Edwards et al. |
| 5,683,366 A | | 11/1997 | Eggers et al. |
| 5,697,882 A | | 12/1997 | Eggers et al. |
| 5,769,843 A | | 6/1998 | Abela et al. |
| 5,807,388 A | | 9/1998 | Jeevanandam et al. |
| 5,827,203 A | | 10/1998 | Nita |

(List continued on next page.)

FOREIGN PATENT DOCUMENTS

| | | |
|---|---|---|
| DE | 296 09 350 U1 | 10/1995 |
| DE | 195 37 084 A1 | 4/1997 |
| WO | WO 96/35469 | 11/1996 |
| WO | WO 97/29701 A1 | 8/1997 |
| WO | WO 97/29803 | 8/1997 |
| WO | WO 97/32551 | 9/1997 |
| WO | WO 97/44071 | 11/1997 |
| WO | WO 98/19614 | 5/1998 |
| WO | WO 98/30144 | 7/1998 |
| WO | WO 98/33557 | 8/1998 |
| WO | WO 99/07296 | 2/1999 |
| WO | WO 00/16704 A1 | 3/2000 |
| WO | WO 00/18305 A1 | 4/2000 |
| WO | WO 01/97698 A1 | 12/2001 |

OTHER PUBLICATIONS

US 6,290,698, 9/2001, Wentzel et al. (withdrawn)
Abstract entitled "Transventricular Revascularization by Laser", Lasers in Surgery and Medicine, 1982, 1 page.
Abstract entitle "Analysis of Protoproducts, Free Radicals and Particulate Debris Generated During In–Vivo Argon Laser Myoplasty", Lasers in Surgery and Medicine, 1991, 1 page.
Isner, J., "Right Ventricular Myocaradial Infarction", The Journal of the American Medical Association, V259, N5, Feb. 5, 1988, 12 pages.
Abstract entitled "Proliferative Activity in Peripheral and Coronary Atherosclerotic Plaque . . . ", J. Clin. Invest., Apr., 1993, 1 page.

(List continued on next page.)

Primary Examiner—Steven J. Ganey
(74) Attorney, Agent, or Firm—Christensen O'Connor Johnson Kindness PLLC

(57) ABSTRACT

A method and device for improving blood circulation to an area of interest within a patient' heart is described. The method comprises inserting a guidable elongated flexible ultrasound device into a patient's vasculature, applying ultrasonic energy to an area in need of improved circulation, and injecting materials such as angiogenic materials or contrasting agents into the area of interest. The device, suitable for performing the method, comprises an elongated tubular body, a distal head of the elongated tubular body for introducing ultrasonic energy to an area of interest, and a needle to deliver materials to an area of interest.

14 Claims, 3 Drawing Sheets

U.S. PATENT DOCUMENTS

| | | | |
|---|---|---|---|
| 5,840,059 A | 11/1998 | March et al. | |
| 5,860,951 A | 1/1999 | Eggers et al. | |
| 5,873,855 A | 2/1999 | Eggers et al. | |
| 5,889,915 A | 3/1999 | Hewton | |
| 5,893,848 A | 4/1999 | Negus et al. | |
| 5,911,729 A | 6/1999 | Shikhman et al. | |
| 5,944,716 A | 8/1999 | Hektner | |
| 5,971,980 A | 10/1999 | Sherman | |
| 6,004,269 A | 12/1999 | Crowley et al. | |
| 6,063,082 A | 5/2000 | DeVore et al. | |
| 6,095,981 A | 8/2000 | McGahan | |
| 6,102,867 A | 8/2000 | Dietz et al. | |
| 6,224,566 B1 * | 5/2001 | Loeb | 604/22 |
| 6,286,512 B1 | 9/2001 | Loeb et al. | |
| 6,287,297 B1 | 9/2001 | Woodruff et al. | |
| 6,290,709 B1 | 9/2001 | Ellis et al. | |
| 6,309,370 B1 | 10/2001 | Haim et al. | |
| 6,312,402 B1 * | 11/2001 | Hansmann | 604/22 |

OTHER PUBLICATIONS

A. Vineberg et al., "Creation of Intramyocardial Pathways to Channel Oxygenated Blood Between Ventricular Arteriolar Zones", Canad. Med. Assoc. Journal, Feb. 4, 1967, vol. 96, pp. 277–279.

A. Vineberg, M.D., "Results of 14 Years' Experience in the Surgical Treatment of Human Coronary Artery Insufficiency", Canad. Med. Assoc. Journal, Feb. 13, 1965, vol. 92, pp. 325–332.

A. Vineberg et al., "The Ivalon Sponge Procedure for Myocardial Revascularization", Surgery, vol. 47, No. 2, Feb., 1960, pp. 268–289.

A. Vineberg et al., "Investigative Surgery: Treatment of Acute Myocardial Infarction by Endocardial Resection", Surgery, vol. 57, No. 6, Jun., 1965, pp. 832–835.

P. Walter et al., "Treatment of Acute Myocardial Infarction by Transmural Blood Supply From the Ventricular Cavity", Europ. Surg. Res., 3:130–138 (1971).

H.A. Khazei et al., "Myocardial Canalization: New Method of Myocardial Revascularization", The Annals of Thoracic Surgery, vol. 6, No. 2, Aug., 1968, pp. 163–171.

J. Hershey et al., "Transmyocardial Puncture Revascularization: a Possible Emergency Adjunct to Arterial Implant Surgery", Geriatrics, Mar., 1969, pp. 101–108.

Press Release dated Oct. 21, 1996, entitled "Doctors Demonstrate Proof of Blood Flow Through Open TMR Channels Created with PLC Systems . . . ", PLC Systems, Inc., 1 page.

Press Release dated Oct. 10, 1996, entitled Texas Fieart Institute Presents Study Comparing the Use of CO2, Holmrum and Excimer Laser for TMR, 1 page.

M.L. Goldman et al., "Nonperative Portacaval Shunt in Swine", Investigative Radiology, vol. 25, No. 5, May 1990, pp. 574–578.

* cited by examiner

ULTRASOUND METHOD FOR REVASCULARIZATION AND DRUG DELIVERY

BACKGROUND OF THE INVENTION

1. Technical Field of the Invention

The present invention relates generally to medical devices for generating an angiogenic response in an interior wall of the heart using a percutaneous myocardial revascularization (PMR) procedure. More specifically, the present invention relates to an intravascular ultrasound PMR device having a needle for supplying the heart with an angiogenic material or contrasting agent.

2. Description of the Prior Art

There is a great deal of interest in improving the methods for treating cardiovascular disease. Traditionally, cardiovascular disease has been treated using procedures such as cardiovascular bypass surgery, coronary angioplasty, laser angioplasty and atherectomy. These techniques generally are aimed at bypassing or opening lesions in coronary vessels so as to restore and increase blood flow to the heart. In some patients, the number of lesions is so great, or the location so remote in the patient's vasculature that restoring blood flow to the heart muscle is difficult. Therefore, it is often the case that cardiovascular disease requires alternative treatment such as percutaneous myocardial revascularization (PMR).

PMR was developed as a less invasive alternative to bypass surgery. PMR was inspired in part by observations that reptilian hearts are supplied primarily by blood perfusing directly from within heart chambers. In contrast, coronary vessels receiving blood from the aorta supply the human heart. PMR is performed by boring channels directly into the myocardium. This can be accomplished by a number of means including the insertion of a flexible catheter through the vasculature into the heart and boring holes into the myocardium. Positive results have been demonstrated in some human patients receiving these types of PMR treatments. These results are believed to be caused in part by increased blood flowing from within a heart chamber through channels formed by PMR to the myocardial tissue. Increased blood flow to the myocardium is also believed to be caused in part by the healing response to wound formation. Specifically, the formation of new blood vessels is believed to occur in response to the newly created wound.

Suitable PMR holes have been burned by laser, cut by mechanical means, removed by ultrasound devices, and burned by radio frequency current devices in a technique called radio frequency percutaneous myocardial revascularization (RF-PMR). In addition, catheter based needle injections of an angiogenic material directly into the myocardium has been developed in conjunction with RF-PMR. U.S. Pat. No. 6,063,082 to DeVore et al. entitled "Percutaneous Myocardial Revascularization Basket Delivery System and Radiofrequency Therapeutic Device" discloses a method in which an angiogenic material can be delivered into a hole recently burned by RF current delivered through the needle. Unfortunately, in this method the angiogenic material may seep out of the hole created by the RF-PRM electrode, thus reducing the effectiveness of the angiogenic material.

U.S. Pat. No. 5,827,203 to Nita entitled "Ultrasound system and Method For Myocardial Revascularization" discloses a method that uses ultrasonic energy to accomplish PMR. Ultrasound PMR offers advantages over other PMR techniques in that the method is less invasive and that in some embodiments no tissue needs to be removed. The application of ultrasonic energy to an area of interest produces a thrombus required for angiogenesis without rupturing endocardial tissue. However, this method currently lacks the ability to deliver additional interventions, such as the delivery of angiogenic materials, to an area of interest. Thus, physicians are limited in their ability to use this method and are required to form channels in the heart wall if massaging an area of interest does not produce the desired effect. Further, if massaging an area of interest is insufficient to induce myocardial revascularization, the ultrasound device is used to bore channels. By including a means for delivering angiogenic materials, the need for using the ultrasound device to bore channels should be reduced.

New research conducted by the applicant suggests that the thrombus, caused by the application of ultrasonic energy, in and around the injury site contains the natural growth factors which cause the angiogenic response. Therefore, destruction of heart tissue, as with RF-PMR, may not be necessary to invoke an angiogenic response. Consequently, there is a need for a method of PMR that creates a natural angiogenic response without creating unnecessary injury to an area of interest. Additionally, it would be beneficial for this method to be able to deliver additional angiogenic material to an area of interest in order to minimize both the destruction of cardiac tissue and seepage.

SUMMARY OF THE INVENTION

A preferred embodiment of the present invention provides a minimally invasive device for the treatment of cardiovascular disease via ultrasound myocardial revascularization that additionally provides means for direct delivery of angiogenic materials. Combining ultrasound myocardial revascularization with an additional lumen for the delivery of angiogenic materials offers advantages over the prior art. Since it is believed that the thrombus contains the natural growth factors capable of facilitating an angiogenic response, this invention can accentuate the body's own natural healing ability without destroying tissue. Further, since no myocardial tissue is destroyed, seepage of angiogenic materials is minimized. Finally, a contrasting agent can be delivered through the needle to enable the physician to image an area of interest.

In one embodiment of this invention, a needle is attached to the ultrasound PMR device adjacent to the catheter along the catheter's longitudinal axis. Angiogenic materials or a contrasting agent can be delivered to an area of interest through the needle.

In another embodiment, the needle passes through the lumen of the ultrasound catheter. Angiogenic materials or a contrasting agent can be delivered to an area of interest through the needle.

DETAILED DESCRIPTION OF THE PREFERRED EMBODIMENTS

Figure 1:
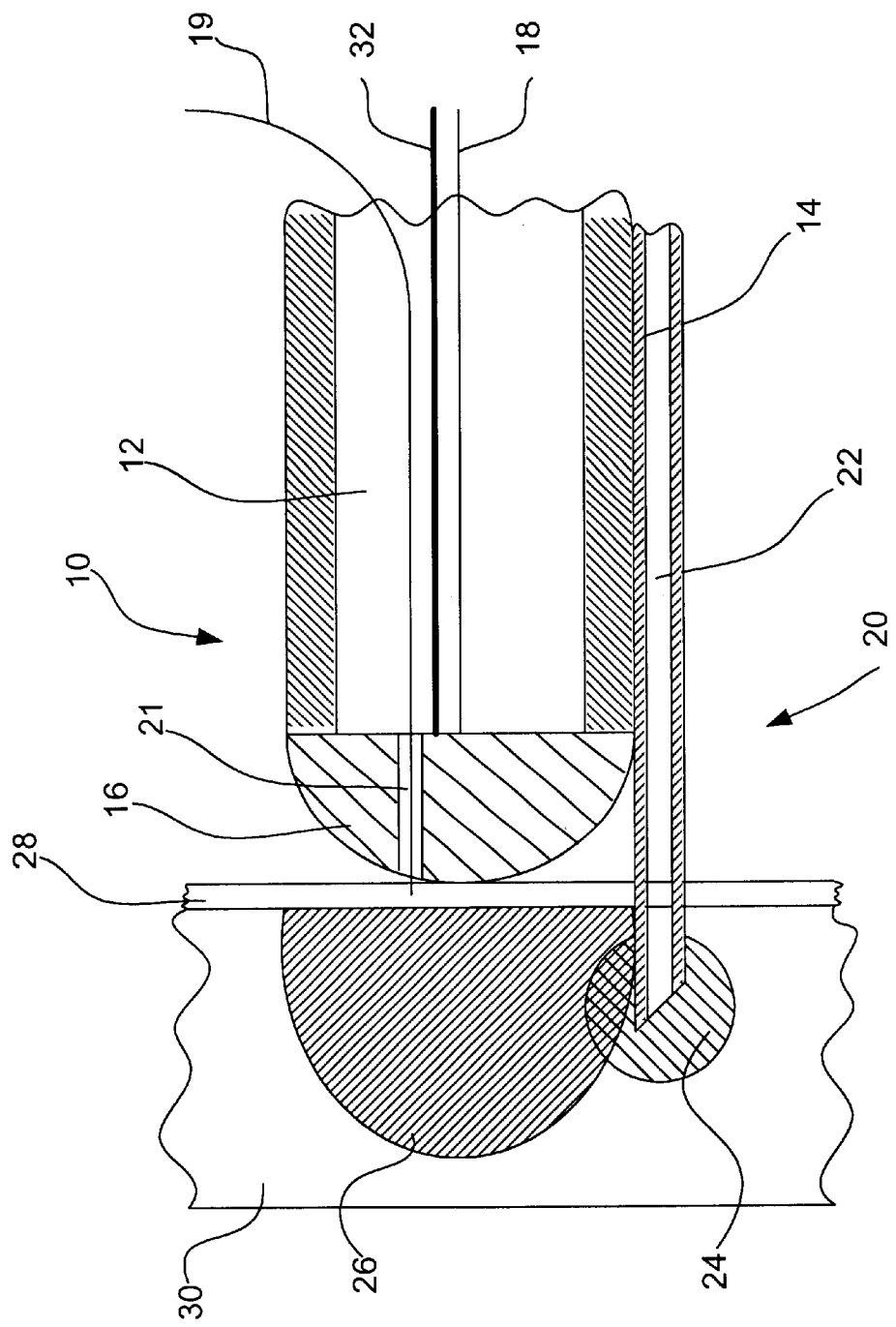
FIG. 1 is a perspective view of an ultrasound PMR catheter system wherein a needle is attached adjacent to the ultrasound catheter along the catheter's longitudinal axis.

Referring now to the drawings wherein like reference numerals refer to like elements throughout the several views, FIG. 1 illustrates a guidable elongated flexible ultrasound device for increasing blood circulation to an area of interest within the heart of a patient. The guidable elongated flexible ultrasound device includes an elongated tubular body 10 with a proximal end closest to the outside of the body and a distal end closest to an area of interest within a patient's heart. In the preferred embodiment, the elongated tubular body 10 is constructed of flexible material to easily pass through turns of the vasculature. The elongated tubular body 10 has at least one lumen 12, extending along the longitudinal axis 14 thereof.

The distal head 16 of the elongated tubular body includes an ultrasonic catheter device that can be connected to a signal generator by an ultrasound transmission lead 18. As such, when a signal generator sends ultrasonic energy through the ultrasound transmission lead 18, ultrasonic energy will pass through the distal head 16 to an area of interest and can be used to massage the myocardium 30. More specifically, the ultrasound transmission lead 18 serves to transmit ultrasonic energy from the proximal end of the elongated flexible ultrasound device to the distal head 16 of the elongated tubular body 10, and then to an area of interest.

The guidable elongated flexible ultrasound device can reach an area of interest by first inserting a guidewire 19 into the patient's vasculature and passing the elongated tubular body 10 over said guidewire 19. In the preferred embodiment, the guidewire 19 can pass through a lumen within the elongated tubular body ranging from the elongated tubular body's far proximal end through the distal head and then through a lumen 21 within said distal head. One skilled in the art can insert the guidewire 19 through a patient's vasculature and into the patient's heart to an area of interest. Then, the elongated tubular body 10 can be passed over said guidewire 19 through a lumen therein to an area of interest.

Mounted adjacent to the elongated tubular body 10 is a needle 20 with a lumen 22 for injecting material 24 near a thrombus 26. In the preferred embodiment, the needle is constructed of stainless steel. The lumen 22 of the needle 20 is of sufficient diameter to allow passage of angiogenic materials or contrasting agents. Angiogenic materials comprise a plethora of substances including but not limited to pharmaceutically active compounds, nucleic acids (including polynucleotide sequences), peptides (including polypeptides and proteins), oligonucleotides, ribozymes, anti-sense genes, DNA compacting agents, and gene/vector systems (i.e., anything that allows for the uptake and expression of nucleic acids).

For example, nucleic acids that may comprise angiogenic materials include antisense DNA and RNA, DNA coding for an anti-sense RNA, or DNA coding for tRNA, or rRNA to replace defective or deficient endogenous molecules. The angiogenic polynucleotides may also code for therapeutic peptides, polypeptides and proteins. A polypeptide is understood to be any translational product of a polynucleotide regardless of size, and whether glycosylated or not.

Therapeutic polypeptides that may act as angiogenic factors including acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; thymidine kinase ("TK") and other agents useful for interfering with cell proliferation, including agents for treating malignancies; and combinations thereof.

In another embodiment of the present invention, angiogenic materials may include a viral vector having linked thereto an exogenous nucleic acid sequence. "Exogenous nucleic acid sequence" is used herein to mean a sequence of nucleic acids that is exogenous to the virus from which the vector is derived. The concentration of the viral vector, preferably an adenoviral vector, is at least about $10^{10}$ plaque forming units ("p.f.u."), or limited by the concentration that results in an undesirable immune response from a patient.

Contrasting agents comprise substances including but not limited to those that enable a physician performing the method or using the device to accumulate information useful for completing or evaluating the procedure. Example of contrasting agents include but are not limited to saline (0.9% NaCl) that can flood the tip of the guidable elongated flexible ultrasound device so as to enable visualization of an area of interest or the device's location within the vasculature, radioactive or radiolabeled magnetic compounds useful for tracing during or after performing the method, and anti-thrombin or blood thinning compounds (including heparin, heparin derivatives, urokinase, dextrophenylalanine proline arginine chloromethylketone, rapamycin, probucol, and verapamil).

Applying ultrasonic energy to the endocardial layer 28 of the myocardium 30 generates the thrombus 26. One skilled in the art can massage the myocardium 30 with ultrasonic energy emitted through the distal head 16 of the elongated tubular body 10. When ultrasonic energy is applied to the myocardium 30, it causes relaxation of the cardiac muscle and vasodilation (relaxation of the vasculature that may result in increased blood flow to the area wherein ultrasonic energy is used upon). In an embodiment of the invention, when the myocardium 30 is massaged, preferably no heart tissue or an insignificant amount is removed from the endocardium 28. A sufficient amount of massaging can lead to the formation of at least one thrombus 26 wherein blot clotting and wound healing can take place and lead to myocardial revascularization. Once a thrombus is formed, the needle 20 can be used to deliver angiogenic materials or contrasting agents that may accentuate the body's natural ability to promote revascularization and/or wound healing.

The guidable elongated flexible ultrasound device also includes an endoscopic visualization device 32 for visualizing an area of interest. The device extends longitudinally through the lumen 22 of the elongated tubular body 10 and comprises an outer sheath having at least one image transmitting optical fiber bundle and possibly one or more additional fiber bundles extending longitudinally throughout. The image transmitting optical fiber bundle in encircled by a plurality of light transmitting optical fiber bundles that also extend longitudinally along the outer sheath. At its proximal end, the visualization device is connected to at least one machine that may be suitable for allowing a physician skilled in the art to visualize an area of interest or the present location within the vasculature of the guidable elongated flexible ultrasound device.

Figure 2:
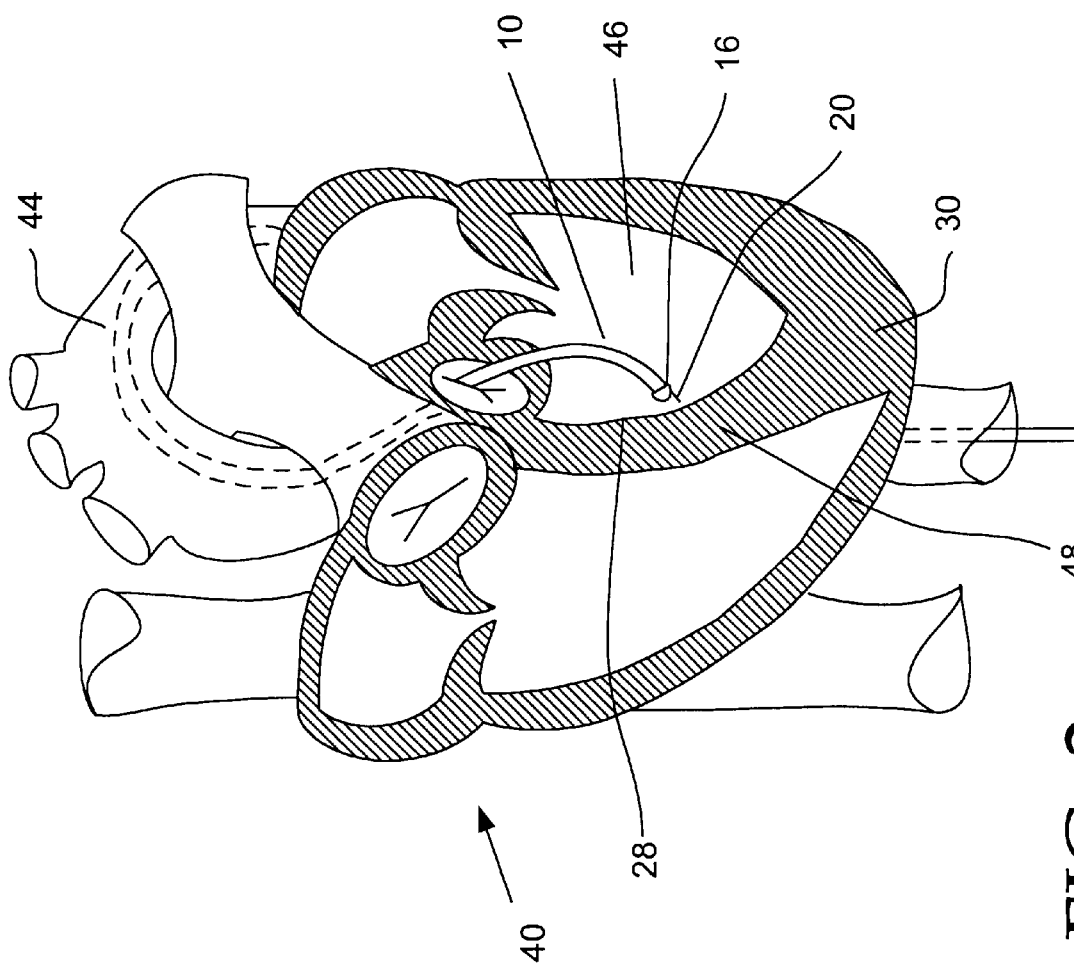
FIG. 2 is a schematic section of a human heart showing percutaneous revascularization of the myocardium according to the present invention.

FIG. 2 illustrates a schematic of a human heart 40 showing percutaneous revascularization of the myocardium 30 using the invention drawn in FIG. 1. The distal head 16 of the elongated tubular body 10 is inserted percutaneously into a major blood vessel (such as the femoral arterial or another peripheral vessel), into and through the aorta 44 to the heart 40, and into a ventricle 46 to an area in need of increased blood circulation 48. Ultrasonic energy from the distal head 16 is used to massage an area of interest so as to generate a thrombus. Angiogenic materials or contrasting agents can then be injected through the needle 20 mounted adjacent to the elongated tubular body 10 through the endocardium 28 and into or near the thrombus.

Figure 3:
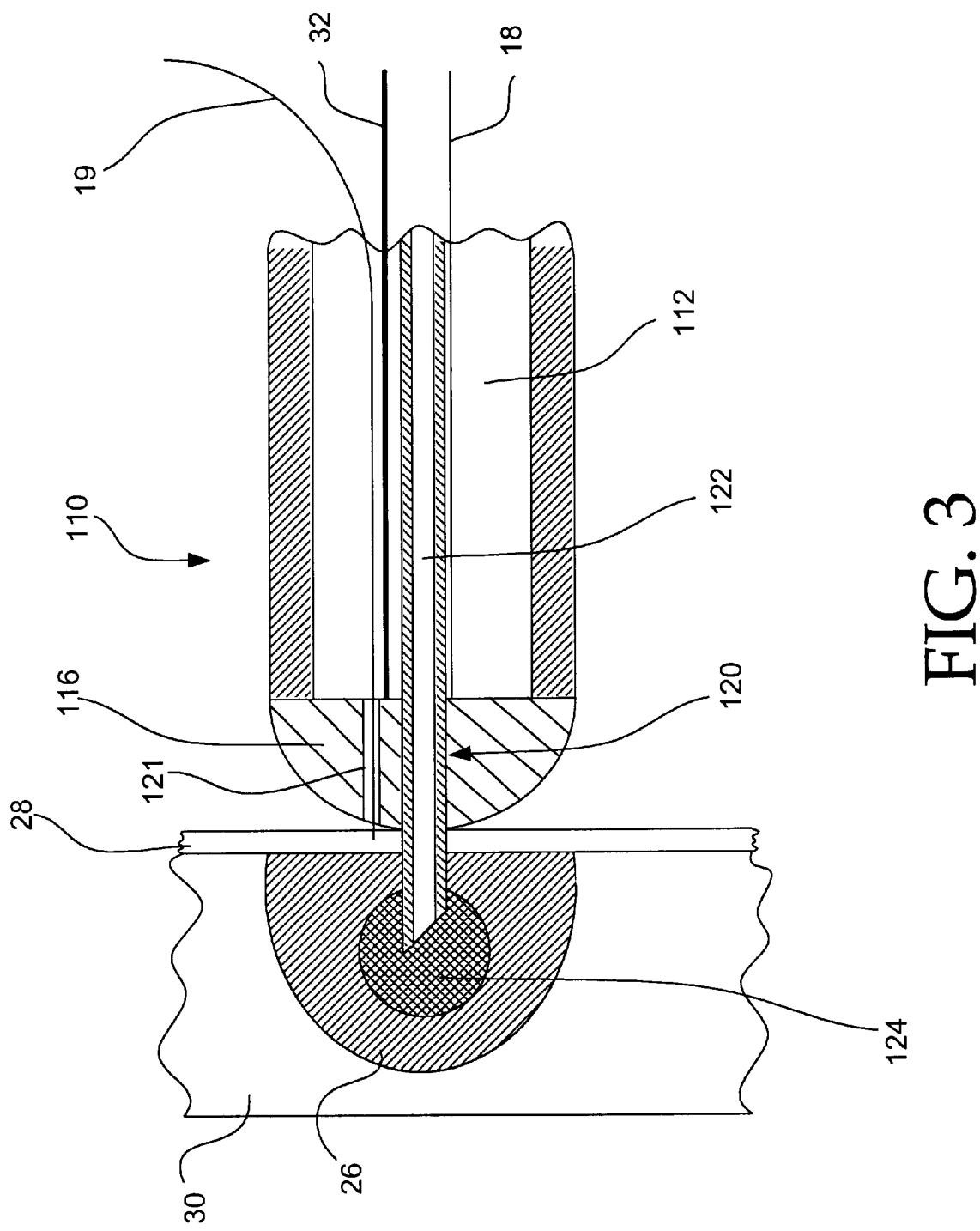
FIG. 3 is a perspective view of an ultrasound PMR catheter system wherein a needle is attached within the lumen of the ultrasound catheter.

FIG. 3 illustrates an embodiment of a guidable elongated flexible ultrasound device similar to that drawn in FIG. 1. The guidable elongated flexible ultrasound device includes an elongated tubular body 110 with at least one lumen 112, with a proximal end closest to the outside of the body and a distal end closest to an area of interest within a patient's heart. The distal head 116 of the elongated tubular body includes an ultrasonic catheter device that can be connected to a signal generator by an ultrasound transmission lead 18. Ultrasonic energy can pass through the distal head 116 via the ultrasound transmission lead to an area of interest and can be used to massage the myocardium 30. A sufficient amount of massaging can lead to the formation of at least one thrombus 26 wherein blot clotting and wound healing can take place and lead to myocardial revascularization.

The guidable elongated flexible ultrasound device also includes an endoscopic visualization device 32 for visualizing said area of interest. The device extends longitudinally through the lumen 122 of the elongated tubular body 110 and comprises an outer sheath having at least one image transmitting optical fiber bundle and possibly one or more additional fiber bundles extending longitudinally throughout. At its proximal end, the visualization device can be connected to at least one machine suitable for allowing a physician skilled in the art to visualize an area of interest or the present location within the vasculature of the guidable elongated flexible ultrasound device.

The guidable elongated flexible ultrasound device can reach an area of interest by first inserting a guidewire 19 into the patient's vasculature and passing the elongated tubular body 110 over said guidewire 19. In the preferred embodiment, the guidewire 19 can pass through a lumen within the elongated tubular body ranging from the elongated tubular body's far proximal end through the distal head and then through a lumen 121 within said distal head. Then, the elongated tubular body 110 can be passed over said guidewire 19 through a lumen therein to an area of interest.

In the current embodiment, a needle 120 for injecting materials 124 into or near a thrombus 26 is mounted within the lumen 112 of the elongated tubular body 110 and passes through the distal head 116. The distal head 116 still retains its ability to transmit ultrasonic energy so as to generate at least one thrombus 26 within the myocardium 30. The lumen 122 of the needle 120 is of sufficient diameter to allow passage of angiogenic materials or contrasting agent. Angiogenic materials may include pharmaceutically active compounds, nucleic acids (including polynucleotide sequences), peptides (including polypeptides and proteins), oligonucleotides, ribozymes, anti-sense genes, DNA compacting agents, and gene/vector systems (i.e., anything that allows for the uptake and expression of nucleic acids) including but not limited to those listed previously. Contrasting agents may include saline, radioactive compounds, and anti-thrombin compounds including but not limited to those listed previously.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A method for improving blood circulation to an area of interest in a heart muscle of a patient, said method comprising the steps of:

inserting a guidable elongated flexible ultrasound device into said patient's vasculature, said guidable elongated flexible ultrasound device having an elongate lumen, a distal end, a proximal end, a distal head mounted on said distal end, and a needle mounted to said elongated tubular flexible ultrasound device in fluid communication with said elongate lumen;

guiding said distal head to said area of interest in said heart muscle;

applying ultrasonic energy via said distal head to said area of interest to form a thrombus without removing any heart material from the area of interest; and injecting a material into said thrombus with said needle.

2. The method of claim 1, wherein said material is an angiogenic material.

3. The method of claim 1, wherein said material is a contrasting agent.

4. The method of claim 1, wherein the step of applying said ultrasonic energy further comprises the step of massaging said area of interest without removing any portion of said heart muscle at said area of interest.

5. The method of claim 1, wherein said needle is attached adjacent to said distal head.

6. The method of claim 1, wherein said needle extends from said distal head.

7. The method of claim 1, wherein the step of inserting said guidable elongated flexible ultrasound device further comprises the step of inserting a guidewire into said patient's vasculature and passing said guidable elongated flexible ultrasound device over said guidewire.

8. The method of claim 1, wherein said guidable elongated flexible ultrasound device includes an endoscopic visualization device for visualizing said area of interest.

9. A method for improving blood circulation to an external area of interest in a heart muscle of a patient, said method comprising the steps of:

providing a guidable elongated flexible ultrasound device into said patient's chest cavity, said guidable elongated flexible ultrasound device having an elongate lumen, a distal end, a proximal end, a distal head mounted on said distal end, and a needle with a lumen mounted to said elongated tubular flexible ultrasound device in fluid communication with said elongate lumen;

guiding said distal head within said patient's chest cavity to contact said exterior area of interest of said heart muscle;

applying ultrasonic energy via said distal head to said external area of interest to form a thrombus without removing any heart material from the area of interest; and injecting a material into said thrombus with said needle.

10. The method of claim 9, wherein said material is an angiogenic material.

11. The method of claim 9, wherein said material is a contrasting agent.

12. The method of claim 9, wherein the step of applying said ultrasonic energy further comprises the step of massaging said external area of interest without removing any portion of said heart muscle at said external area of interest.

13. The method of claim 9, wherein said needle is attached adjacent to said distal head.

14. The method of claim 9, wherein said needle extends from said distal head.

* * * * *